United States Patent [19]

Irion et al.

[11] Patent Number: 5,058,568
[45] Date of Patent: Oct. 22, 1991

[54] FLEXIBLE ENDOSCOPE

[75] Inventors: Klaus Irion, Emmingen-Liptingen; Horst Dittrich, Immendingen; Hans-Peter Schwarz, St. Ingbert, all of Fed. Rep. of Germany

[73] Assignee: Karl Storz GmbH & Co., Fed. Rep. of Germany

[21] Appl. No.: 459,719

[22] PCT Filed: May 28, 1989

[86] PCT No.: PCT/DE89/00328
§ 371 Date: Jan. 26, 1990
§ 102(e) Date: Jan. 26, 1990

[87] PCT Pub. No.: WO89/11242
PCT Pub. Date: Nov. 30, 1989

[30] Foreign Application Priority Data

May 26, 1988 [DE] Fed. Rep. of Germany ....... 3817915

[51] Int. Cl.$^5$ .............................................. A61B 1/00
[52] U.S. Cl. .................................................... 128/4
[58] Field of Search ........................................ 128/4, 6

[56] References Cited
U.S. PATENT DOCUMENTS 4,327,711  5/1982  Takugi .................................. 128/4
4,615,330  10/1986  Nagasaki et al. ...................... 128/4

Primary Examiner—William H. Grieb
Attorney, Agent, or Firm—Evenson, Wands, Edwards, Lenahan & McKeown

[57] ABSTRACT

A flexible endoscope has at least one outer protective coat, one protective mesh and elements arranged in the distal region, which are connected via a series of connecting lines for data and/or energy transmission to the connection element arranged at the opposite end. The mesh includes a plurality of conductive lines which are electrically insulated from each other. The connecting lines are included among the conducting lines of the mesh.

16 Claims, 1 Drawing Sheet

FLEXIBLE ENDOSCOPE

DESCRIPTION

1. Technical Field

The present invention relates to a flexible endoscope having at least one outer protective casing, at least one protective mesh including elements arranged in the distal region, which are connected via a series of connecting lines for data and/or energy transmission to a connection element arranged at the opposite end.

2. State of the Art

Flexible endoscopes having at least one outer protective casing and one protective mesh have been known for quite some time. Due to the progress made in recent years in miniaturizing sensor arrays, it has become possible to integrate, by way of illustration an ultrasound array having a plurality of ultrasound transmitters and receivers in the distal end of a flexible endoscope.

Furthermore, it has been suggested a number of times to provide, by way of illustration, CCD video recorders in the region of the distal end of the endoscopes.

Moreover, a great variety of designs of therapy elements, such as coagulation elements of an optical or electric nature, as well as diagnostic elements arranged in the distal end and requiring electric supply and signal lines or lightwave conductors for operation, have been suggested for therapeutic applications.

All flexible endoscopes of this type have in common that the elements arranged in the distal region have to be connected via a series of electric lines to one or several connection elements arranged in the so-called proximal region.

In accordance with the state of the art, these lines, which establish the electric connection between elements arranged in the distal region and the proximal region of the endoscope, are guided in the so-called "free lumen" of the endoscope. The free lumen is the part of the cross-section of the endoscope which is empty space, and is therefore available for the accommodation of useful elements, such as (additional) image transmission fibers, illumination devices, medical instruments and the like.

If a great number of electric lines are required, as is the case, by way of illustration, for the arrangement of a series of ultrasound transducers for recording an ultra sound image, the available "free lumen" is greatly diminished for other elements by the electric lines.

DESCRIPTION OF THE INVENTION

The object of the present invention is to improve a flexible endoscope, in which a series of connecting lines for data and/or energy transmission are laid between the distal end region and the proximal end region, in such a manner that the available free lumen is practically not restricted, respectively reduced.

A solution and its further embodiments in accordance with the present invention to the aforegoing object is described in the claims hereto.

The present invention is based on the fundamental concept that the elements necessarily present on an endoscope, such as protective mesh, support spirals and/or cable lines, are designed as connecting lines. Connecting lines are understood to be electric lines as well as optical lines.

In endoscopes having a great number of electric lines, it is advantageous to employ the electric lines as the protective mesh between the outer protective casing and, by way of illustration, the support spirals.

Ten to several hundred electric lines can be realized in this protective mesh without much difficulty.

In this event, the electric lines may be normal insulated lines which, by way of illustration, are made of thin copper wire and a teflon insulation.

However, it is advantageous, particularly if HF (high frequency) signals are to be transmitted via the electric lines if the electric lines are co-axial lines.

In any case, however, it is advantageous if the protective mesh is arranged in a known manner between the outer protective casing and a support spiral hose. This design has the advantage that the diameter of the protective mesh is comparatively large. As a result, on the one hand, the radius of curvature of the individual lines is not too small in plaiting and therefore there is no danger of line breakage due to bending. On the other hand, a great number of lines can be accommodated in the protective mesh.

In any event, however, it is especially advantageous if the protective mesh is designed in such a manner that it has a large overlapping cover. In this way a large bending angle is warranted so that unimpeded work with an endoscope designed in accordance with the present invention is possible even if the protective mesh is designed with co-axial lines.

While a preferred embodiment of the invention will be described in which lines making up the protective mesh are used for conducting electrical signals, the inventive fundamental concept may be more broadly defined to utilize any elements which are or could be conductive and are already present in a flexible endoscope for conducting electrical signals.

For instance, it is possible to utilize the support spirals which are usually present in flexible endoscopes, and the tackles present in the endoscope as electrical conductors. Since these elements have comparatively large cross-sections, they may be employed as supply lines for comparatively great current strengths as required by devices such as electric coagulators.

It is also possible to execute the tackles especially in HF applications as co-axial lines or, if necessary, as a lightwave conductor encased in a protective spiral.

It is possible, by way of illustration, to use the invented design in a flexible endoscope in which the elements arranged in the distal end region compose an electronic image recorder or there are a great number of ultrasound transducers in the distal end region.

BRIEF DESCRIPTION OF THE DRAWING

The present invention is made more apparent using a preferred embodiment with reference to the accompanying drawing, in which depict.

DESCRIPTION OF A PREFERRED EMBODIMENT

Figure 1:
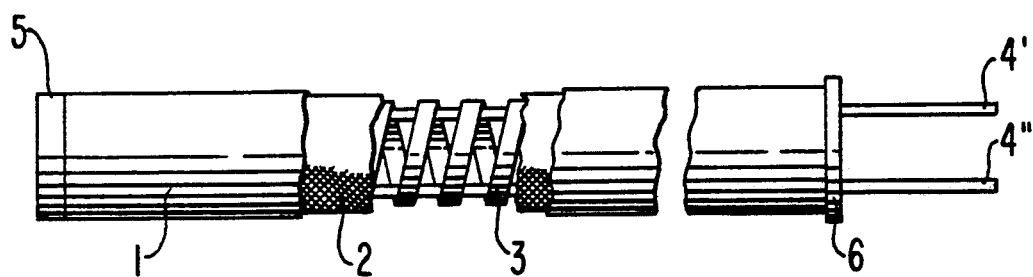
FIG. 1 a partial cross-section of an invented flexible endoscope.

FIG. 1 shows an endoscope designed in accordance with the present invention. This endoscope is composed in a known manner of an outer protective casing 1, a protective mesh 2 arranged beneath this protective casing, and an inner support spiral hose 3. Inside the spiral hose 3 is the free lumen of the flexible endoscope. The free lumen may be used for laying out depicted optical fibers for image transmission and illumination, instruments, etc. Furthermore, depending on the specific application, scavenging lines for a scavenging fluid, exhaust lines, etc., are laid in this free lumen. In addition, the illustrated preferred embodiment is provided with two tackles flexure controlling wires 4' and 4" for operating the flexible endoscope.

Furthermore, an array 5 is arranged in the distal region. The array 5 may, by way of illustration, be an ultrasound transducer array of ultrasound transmitters, and receivers uniformly set up.

In order to trigger the individual transducer elements and to read out the ultrasonic signals received by the elements, it is necessary to lay a great number of electric lines between the array 5 arranged in the distal end region and the proximal end 6 of the flexible endoscope.

In conventional endoscopes, the electric lines are laid in the free lumen inside the support spiral hose 3. In accordance with the present invention, these lines make up the protective mesh 2.

Figure 2:
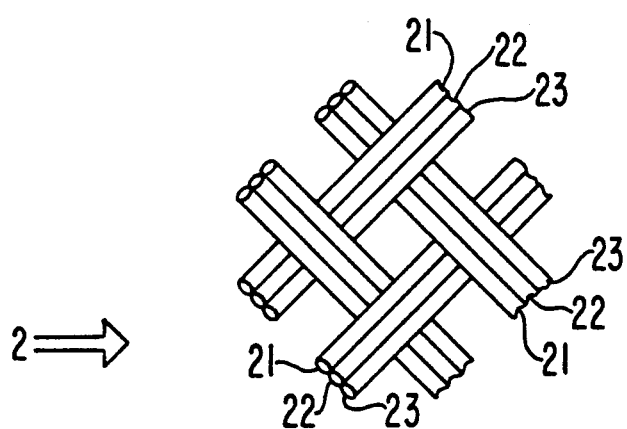
FIG. 2 a top view of a protective mesh designed in accordance with the present invention.

FIG. 2 shows a preferred embodiment for such a protective mesh 2 composed of electric lines. Each single "thread" of the protective mesh 2 in the illustrated preferred embodiment, "woven" in a known manner, is composed of three electric lines each 21, 22, 23 built up in a strip line. Each single line 21, 22, or 23 may be in an insulated line built up in a conventional manner or in a co-axial line. The lines 21 to 23 gathered in a strip line are interlaced in such a way that the yielded overlapping cover permits a great bending angle of the endoscope. Thus the usual work with a flexible endoscope is not impeded by the invented design. In particular, the flexible endoscope does not become rigid due to the design of the protective mesh with electric lines than the prior art flexible endoscopes are.

It is also possible to design only the warp or the weft of the mesh as electric lines. Nonetheless, a great number of electric lines can be accommodated without diminishing the free lumen. By way of illustration, depending on the diameter of the flexible endoscope and the design of the protective mesh, between ten and several hundred lines can be integrated in the protective mesh.

In the foregoing the present invention has been described using a preferred embodiment without the intention of limiting the scope of the overall inventive concept - to utilize elements which are already present in a flexible endoscope as connecting lines. Naturally, there are many different alterations or modifications possible within this overall inventive concept.

By way of illustration, it is possible to design the support spiral hose 3 and/or the tackles 4' and 4" as electric (or optical) lines instead of or in addition to the protective mesh. Due to its large cross-section area, the support spiral hose 3 is especially suited as an electric line for strong currents as required, by way of illustration, for a coagulation device. Tackles (flexure controlling wires) 4' and 4" are particularly suited as co-axial lines for extreme HF applications or as light conductors or as "light conductors" due to their large diameter.

Depending on the application, it is possible to integrate electric and/or optical lines in other elements of the endoscope, and to design these elements as appropriate lines.

Moreover, the present invention is also not restricted to connecting ultrasound transducers arranged at the distal end with the proximal end. The element or elements arranged in the region of the distal end may consist of other parts such as CCD video chips, coagulation devices or the like.

Furthermore, it is particularly advantageous when the lines are integrated in the protective mesh if single lines are provided as "reserve lines", which can be used instead of damaged lines. This has the advantage that if the damage to the flexible endoscope by which the individual lines are interrupted is small, it is not necessary to repair or replace the endoscope.

In addition, the electric connection may also be constructed "double" from the very start, i.e. to establish the connection between a distal element and the proximal connection by means of two (or more) redundant lines spaced at a distance from each other.

Lines for electric screening may also be integrated in the protective mesh in a known manner, and/or the lines may be laid in such a way that electric disturbances are minimized.

What we claim is:

1. A flexible endoscope comprising:
   at least one outer protective casing,
   at least one protective mesh,
   elements arranged at a distal region of the endoscope,
   a connection element arranged at an opposite end of the endoscope, and
   a series of electrically separate connecting lines for conducting a plurality of data and energy signals to the connection element, wherein said connecting lines compose said protective mesh.

2. A flexible endoscope according to claim 1, wherein said connecting lines are insulated electric lines.

3. A flexible endoscope according to claim 2, wherein said connecting lines are co-axial lines.

4. A flexible endoscope according to claim 3, wherein said connecting lines are lightwave conductors.

5. A flexible endoscope according to claim 4, wherein said protective mesh is arranged between said at least one outer protective casing and a support spiral hose.

6. A flexible endoscope according to claim 5, wherein said protective mesh comprises a cover means for permitting a large bending angle of said endoscope.

7. A flexible endoscope according to claim 6, further comprising a support spiral hose which is an electric spiral line.

8. A flexible endoscope according to claim 7, further comprising tackles which are one of electric and optical lines.

9. A flexible endoscope according to claim 8, wherein single connecting lines are provided as reserve lines.

10. A flexible endoscope according to claim 9, wherein each of the connecting lines comprises at least two spaced lines.

11. A flexible endoscope according to claim 10, wherein each of the connecting lines comprise at least two spaced lines.

12. A flexible endoscope according to claim 11, wherein the elements arranged at the distal region include an electronic image recorder.

13. A flexible endoscope according to claim 12, wherein said elements arranged at the distal region include an ultrasound transducer.

14. A flexible endoscope comprising:
   a support spiral hose which is an electric conductor;
   an electrically conductive protective mesh disposed outside the support spiral hose; and
   means for electrically isolating the support spiral hose from the mesh, whereby the support spiral hose and the mesh may carry a plurality of separate electrical signals.

15. A flexible endoscope according to claim 14, wherein the means for isolating includes an insulator disposed between the support spiral hose and the mesh.

16. A flexible endoscope comprising:
first and second tackles which are one of electric and optical lines for carrying first and second separate signals.

* * * * *